United States Patent [19]

Bevilacqua

[11] Patent Number: 5,693,315

[45] Date of Patent: Dec. 2, 1997

[54] MAMMAL TOOTH TREATING COMPOSITION

[75] Inventor: Al Bevilacqua, Naperville, Ill.

[73] Assignee: Abco Trust, Peotone, Ill.

[21] Appl. No.: 660,864

[22] Filed: Jun. 10, 1996

[51] Int. Cl.[6] ................................................ A61K 7/18
[52] U.S. Cl. ............................................................ 424/52
[58] Field of Search ............................................. 424/52

[56] References Cited

U.S. PATENT DOCUMENTS

| 3,758,689 | 9/1973 | Rapfogel | 514/64.3 |
| 3,956,480 | 5/1976 | Dichter et al. | 424/54 |
| 4,593,054 | 6/1986 | Asmussen et al. | 523/118 |
| 4,906,670 | 3/1990 | Higashi et al. | 514/773 |
| 5,270,031 | 12/1993 | Lim et al. | 424/49 |
| 5,330,746 | 7/1994 | Friedman et al. | 424/49 |
| 5,438,076 | 8/1995 | Friedman et al. | 514/772.6 |

*Primary Examiner*—Alan L. Rotman
*Assistant Examiner*—D. Margaret M. Mach
*Attorney, Agent, or Firm*—Evan D. Roberts

[57] ABSTRACT

A tooth sensitivity treating composition containing hydroxyethyl methacrylate, sodium fluoride, anti,icrobial compound and an inert solvent, with an antidegenerate preserative.

6 Claims, No Drawings

MAMMAL TOOTH TREATING COMPOSITION

BACKGROUND OF THE INVENTION

Mammal tooth sensitivity is a frequent occurrence and, in the past, has been, on occasion, difficult to manage. In this regard, there are two (2) basic mechanisms that can be responsible for this sensitivity, namely: open and unobstructed dentinal tubules and residual bacteria. The number and size of the dentinal tubules normally increase at the tooth cervix and near the pulp chamber. These tubules connect the pulp chamber and pulp tissue with overlying dentin by the odontoblastic process lying within the tubules. When the tubules are numerous, large and/or open, they become more susceptible to transfer of bacteria toxins and/or fluid flow.

One established theory of the cause of dental tooth sensitivity or pain is that rapid fluid shift within the dentinal tubules will elicit pain. Another theory on dentinal hypersensitivity indicates that the sensitivity is caused by residual bacteria and bacteria producing toxins which are an irritant to the dental pulp which, in turn, elicits the pain or sensitivity.

In the past, other systems and/or compositions have been tried with only a limited success. In particular, oxalates, copal varnishes, calcium hydroxide, bonding systems and various products containing potassium nitrate, sodium citrate and strontium chloride. Although some formulas have, in the past, produced varied and limited results, they usually have failed to address all of the issues to substantially prevent the problem causing the sensitivity.

SUMMARY OF THE INVENTION

This invention relates to a composition to be orally applied to mammal teeth to address the cause of sensitivity in the teeth to reduce or eliminate the sensitivity.

An object of this invention is to provide a composition which can be applied directly to mammal teeth to reduce tooth hypersensitivity.

A further object of this invention is to provide a composition that can bond with dentinal protein collagen to aid in preventing tooth hypersensitivity.

Another object of this invention is to provide a strong long-lasting bond between the dentinal protein collagen and hydroxyethyl methacrylate to reduce tooth hypersensitivity.

Another object of this invention is to provide a composition including fluoride to strengthen and reinforce a bond between dentinal protein and hydroxyethyl methacrylate to reduce tooth hyper-sensitivity.

Another object of this invention is to combine an antimicrobial action with a hydrophilic resin that is greatly enhanced by the presence of fluoride.

Another object of this invention is to provide a strong long-lasting bond between the dentinal protein collagen and the hydroxyethyl methacrylate. The fluoride strengthens and reinforces this bond.

DESCRIPTION OF THE INVENTION

The composition of this invention, to provide the optimal performance of reducing dentinal hypersensitivity, contains:

| Raw Material | % W/W |
| --- | --- |
| Hydroxyethyl Methacrylate | 35.00–37.00 |
| Sodium Fluoride | 0.25–0.10 |
| Antimicrobial Compound | .75–20.0 |
| Inert Solvent | Balance |

In addition to the above, an antidegenerate preservative ingredient is preferred in the preferred amount of 0.10% by weight in the balance to prevent ultra-violet energy and other oxidative agents from weakening the composition during its useful life.

One embodiment of the composition of this invention, to provide the optimal performance of reducing dentinal hypersensitivity contains:

| Raw Material | % W/W |
| --- | --- |
| Hydroxyethyl Methacrylate | 36.10 |
| Sodium Fluoride | 0.50 |
| Benzalkonium Chloride | 0.80 |
| $H_2O$ | Balance |

A specific example of an antidegenerate preservative ingredient for this embodiment, in the amount of 0.10% by weight in the balance, is di-tert-butyl para cresol to prevent ultra-violet energy and other oxidative agents from weakening the composition during its useful life.

Another specific embodiment of the composition of this invention that has been found to provide the performance of reducing dentinal hypersensitivity, contains:

| Raw Material | % W/W |
| --- | --- |
| Hydroxyethyl Methacrylate | 36.10 |
| Sodium Fluoride | 0.50 |
| Glutaraldehyde | 0.20 |
| $H_2O$ | Balance |

A specific example of an antidegenerate preservative ingredient for this embodiment, in the amount of 0.10% by weight, is di-tert-butyl para cresol to prevent ultra-violet energy and other oxidative agents from weakening the composition during its useful life.

The composition of this invention is applied to the dentinal tooth structure by using a cotton pellet or brush and can be burnished into the surface to increase its effectiveness. A chemical reaction cross-links the hydroxyethyl methacrylate to the dentin proteins or collagens and dentin proteins to each other. This effectively forms an insolvable organic plug which prohibits flow of liquid through the dentinal tubules to preclude the sensitivity otherwise caused thereby.

The benzalkonium chloride induces bacteria activity that effectively prevents premature loss of the dentin plugs as a result of metabolic activities and the benzalkonium chloride is not an irritant to oral tissue. The fluoride induces a mineralization of the dentin plugs to improve the long term effectiveness of the organic plugs.

Various changes and modifications can be made in the process and products of this invention without departing from the scope thereof. The various embodiments described herein were for the purpose of further illustrating the invention but were not intended to limit it.

What is claimed is:

1. A mammal tooth treating composition which consists of hydroxyethyl methacrylate, sodium fluoride, antimicrobial, an antidegenerate and an inert solvent.

2. A tooth treating composition as defined in claim 1 wherein said antimicrobial is benzalkonium chloride.

3. A tooth treating composition as defined in claim 2 wherein said antidegenerate is di-tert-butyl para cresol.

4. A tooth treating composition as defined in claim 2 wherein said antidegenerate is di-tert-butyl para cresol.

5. A tooth treating composition as defined in claim 1 wherein said antimicrobial comprises glutaraldehyde.

6. A tooth treating composition as defined in claim 5 wherein said antidegenerate comprises di-tert-butyl para cresol.

* * * * *